(12) United States Patent
Tseti

(10) Patent No.: US 8,877,817 B2
(45) Date of Patent: Nov. 4, 2014

(54) STABLE READY TO USE INJECTABLE PARACETAMOL FORMULATION

(76) Inventor: Ioulia Tseti, Kifissia (GR)

(*) Notice: Subject to any disclaimer, the term of this patent is extended or adjusted under 35 U.S.C. 154(b) by 12 days.

(21) Appl. No.: 13/695,785

(22) PCT Filed: May 18, 2011

(86) PCT No.: PCT/EP2011/002482
§ 371 (c)(1),
(2), (4) Date: Apr. 30, 2013

(87) PCT Pub. No.: WO2011/144335
PCT Pub. Date: Nov. 24, 2011

(65) Prior Publication Data
US 2013/0210922 A1  Aug. 15, 2013

(30) Foreign Application Priority Data
May 19, 2010 (EP) ................................ 10005258

(51) Int. Cl.
*A01N 37/18* (2006.01)
*A61K 31/16* (2006.01)

(52) U.S. Cl.
USPC .......................... 514/630; 514/629

(58) Field of Classification Search
USPC ........................................ 514/630
See application file for complete search history.

(56) References Cited

U.S. PATENT DOCUMENTS

| | | | | |
|---|---|---|---|---|
| 6,949,509 | B2* | 9/2005 | Woodrow | 514/10.9 |
| 2004/0045546 | A1* | 3/2004 | Hirsh et al. | 128/200.14 |
| 2009/0246276 | A1* | 10/2009 | Jackson et al. | 424/465 |
| 2010/0322973 | A1* | 12/2010 | Kano et al. | 424/234.1 |

FOREIGN PATENT DOCUMENTS

| | | |
|---|---|---|
| EP | 085329 | 6/2003 |
| WO | WO2009064928 | 5/2009 |
| WO | WO2009098716 | 8/2009 |
| WO | WO 2009098716 A2 * | 8/2009 |

OTHER PUBLICATIONS

Ruchirawat et al., "The Effect of Thiamine Deficiency on the Metabolism of Acetaminophen," Biochemical Pharmacolgy, vol. 30, No. 14, May 19, 1980, pp. 1901-1906.
Kosy et al., "Stability of Aqueous Solutions of N-Acetyl-p-aminophenol," State University of Iowa, college of Pharmacy, Iowa City, Jul. 18, 1960, pp. 113-118.
International Search Report for PCT/EP2011/002482, dated Jun. 11, 2011, 4 pages.

* cited by examiner

Primary Examiner — Layla Soroush
(74) Attorney, Agent, or Firm — Dilworth IP LLC

(57) ABSTRACT

The invention concerns a stable aqueous paracetamol solution for use in IV infusion comprising at least one stabilizing-dissolving compound for paracetamol in solution selected from the group consisting of cyclodextrins, at least one stabilizing compound bearing at least one thiol functional group and at least one stabilizing compound selected from the group consisting of Thiamine salts.

20 Claims, No Drawings

STABLE READY TO USE INJECTABLE PARACETAMOL FORMULATION

The present invention refers to a pharmaceutical composition comprising paracetamol for parenteral administration by IV infusion, with an optimum pH 6.0 (ranging between 5.5 and 6.5) comprising at least one stabilizing-dissolving compound for paracetamol in solution selected from the group consisting of cyclodextrins, at least one stabilizing compound bearing at least one thiol functional group and at least one stabilizing compound selected from the group consisting of Thiamine salts in a suitable concentration, able to stabilize and solubilize the paracetamol even at elevated temperatures.

DESCRIPTION

1. Field of the Invention

The present invention relates to an injectable liquid paracetamol composition according to claim 1, which is stable even at elevated temperatures over a longer period of time.

2. Background of the Invention

Paracetamol is considered to be the main active metabolite of phenacetin and acetanidile having analgesic and antipyretic properties. Paracetamol has equivalent analgesic and antipyretic action to that of aspirin whilst it expresses weak anti-inflammatory action therefore its use in inflammatory rheumatic diseases is limited.

A large number of pharmaceutical preparations to be administered orally or even topically are known. However, it is difficult to obtain a pharmaceutical preparation for injection and particularly, a ready-to-use solution for intravenous perfusion, due to the fact that paracetamol is not very soluble in water and its solutions in aqueous medium are unstable in the presence of oxygen and/or light, being decomposed through a plurality of degradation pathways which are well known and are described for example in the article "Stability of aqueous solutions of N-acetyl-p-amninophenol", by K. T. Koshy and J. L. Lach, J. Pharmaceutical Sciences, Vol 50 (2) (February 1961), p. 113-118. This instability in aqueous medium is shown by the appearance of degradation substances causing a coloring in the solution. The different substances causing the coloring of the solution include benzoquinoimines which are hepatotoxic in humans.

However, the development of color in pharmaceutical solutions and especially in injectable formulations, which must be completely transparent, involves a serious problem, because the presence of said color is indicative of the existence of unwanted compounds in the formulation and therefore leads to the rejection of the injectable product without being used.

One of the causes of paracetamol degradation is based on chemical oxidation reactions in which the oxygen present in the solution is the main precursor of this degradation. The secondary cause of degradation may be the deacetylation of the amino group generating p-aminophenol which is also quickly degraded producing p-benzoquinoneimine. This deacetylation takes places both at acid pH and (much faster) at basic pH once the phenolate form is present.

Obtaining stable paracetamol solutions in aqueous medium can be solved by means of several joint actions.

1) Establishing an optimal pH in which the formation of 4-aminophenol is prevented or minimized, as has been indicated by K. Thomas Koshy and Jon L. Lach in the previous indicated reference "Stability of aqueous solutions of N-acetyl-p-aminophenol", J. of Phar. Sci., Vol 50 No. 2 (1961), 113-118, the hydrolysis of the acetate group of paracetamol is minimized between pH=4.5 and pH 6.0.

2) Preventing the presence of oxygen in solution. This action is described in Spanish patent no. 2,201,316, from the validation in Spain of European patent EP 858,329 B1, issued to Pharmatop SCR. This document discloses a process whereby paracetamol oxidation is prevented by means of eliminating the main element activating the reaction, oxygen, with nitrogen bubbling. By further keeping the solution in a completely hermetic bottle, the stability of paracetamol in solution is ensured for long time periods, with minimal impurity levels and the total absence of color in the solution. It may be presumed that this product of the prior art must be kept in suitable bottles preventing the incorporation of oxygen into the solution and therefore these solutions cannot be stored in individual oxygen-permeable bottles such as plastic materials.

Further, U.S. Pat. No. 6,028,222 discloses the use of free radical antagonists or free radical scavengers, which may be a polyol or an organic compound substituted by one or more thiol functional groups, to provide stable analgesic formulations of paracetamol. U.S. Pat. No. 4,727,064 discloses the use of alkylated cyclodextrins to improve the solubility of drugs, inter alia paracetamol, in water.

Despite the achievements of the prior art, there is due to raising quality and safety requirements a constant need to further improve the stability of aqueous paracetamol solution for use in IV infusion even at elevated temperatures over a longer period of time without the need of keeping the solutions in a completely hermetic bottle.

The present invention therefore concerns a stable aqueous paracetamol solution for use in IV infusion comprising at least one stabilizing-dissolving compound for paracetamol in solution selected from the group consisting of cyclodextrins, at least one stabilizing compound bearing at least one thiol functional group and at least one stabilizing compound selected from the group consisting of Thiamine salts.

The at least one stabilizing-dissolving compound for paracetamol in solution selected from the group consisting of cyclodextrins, the at least one stabilizing compound bearing at least one thiol functional group and the at least one stabilizing compound selected from the group consisting of Thiamine salts are preferably present in a total concentration between 0.001% and 20% m/v.

The stable aqueous paracetamol solution according to the invention may have a pH between 4.0 and 7.0. Typically, the solution may be a buffer with a buffer composition selected from at least one of the acid form and the ionized form of: citric, malic, acetic, sorbic, phosphoric, fumaric, lactic, gluconic and tartaric acids or mixtures thereof. Preferably, the pH is between 5.5 and 6.5 and more preferably the pH is adjusted to 6. A typical buffer includes phosphate or sodium citrate/acetate and is preferably disodium phosphate dihydrate.

The preferred cyclodextrin is a hydroxyalkyl-cyclodextrin, in particular 2-hydroxypropyl-beta-cyclodextrin. Typically, the at least one stabilizing-dissolving compound for paracetamol in solution selected from the group consisting of cyclodextrins is provided in a concentration between 0.2% m/v and 19% m/v, preferably in a concentration between 0.2% m/v and 6.0% m/v and more preferably between 0.5% and 3.0% m/v.

The 2-hydroxypropyl beta-cyclodextrin (HPBCD) is preferably selected from derivatives with a degree of substitution of between 2.5 and 10 hydroxypropyl substituents per beta-cyclodextrin molecule, more preferably between 3.5 and 8 hydroxypropyl substitutents per beta-cyclodextrin molecule.

The molar ratio of Paracetamol to 2-hydroxypropyl beta-cyclodextrin is preferably 100:1 to 0.1:1, more preferably 5:1, most preferably 1.5:1.

The at least one stabilizing compound bearing at least one thiol functional group is selected from the group consisting of thioglycerols, cystein, acetylcycstein, thioglycolic acid and/or salts thereof, dithiothreitol, reduced glutathione, thiolactic acid and/or salts thereof, thiourea and mercaptoethanesulfonic acid and is typically a thioglycerol, preferably monothioglycerol, present in a concentration between 0.001% m/v and 0.2% m/v.

The at least one stabilizing compound selected from the group consisting of Thiamine salts is preferably Thiamine HCl and is preferably present in a concentration between 0.001% m/v and 0.2% m/v.

In addition, the aqueous solution may further comprise other chelating agents or complexing agents. The chelating or complexing agent in solution may be selected from the group consisting of EDTA, nitrilotriacetic acid, ethylenediamine-N,N'-diacetic-N,N'-dipropionic acid, ethylenediamine-tetra (methylene phosphoric acid), 2,2'(ethylenediamino)-dibutyric acid, ethylene glycol bis(2-aminoethylether)-N,N,N',N'-tetra acetic acid, and/or salts thereof, and is preferably EDTA. Preferably the chelating or complexing agent is present in a concentration between 0.001% m/v and 0.2% m/v.

The stable aqueous paracetamol solution according to the invention may further comprise isotonizing agents, preferably sodium chloride.

The stable aqueous paracetamol solution for IV infusion may be sterilized by heat or by filtration.

A typical concentration of paracetamol is between 0.20% and 10% m/v, preferably 0.5% and 1.5% m/v.

The aqueous medium of the solution according to the invention may have been deoxygenated by a water-insoluble inert gas ($N_2$).

The compositions according to the invention will be administered intravenously and they are stable when stored for more than 24 months at room temperature. Moreover, the compositions may be even stable when stored for more than 30 days at elevated temperatures, for example 70° C.

A composition may be prepared in solution and stored in clear glass containers or bottles made of a polymer material such as polyethylene, or in soft material bags made from polyethylene, polyvinylchloride or polypropylene.

The molar ratio of paracetamol to cyclodextrin is preferably 100:1 to 0.1:1, more preferably 5:1 and most preferably 1.5:1.

Typically, the solution comprises 2 mg to 200 mg, preferably more than 5 mg, most preferably 10 mg paracetamol per milliliter solution.

The complexing or chelating agent may comprise 0.001 to 5 mg, preferably 0.0015 to 1 mg, most preferably 0.1 mg per milliliter solution.

Further, the solution comprises typically 2 mg to 150 mg, preferably more than 3 mg, most preferably between 6 mg and 7 mg cyclodextrin per milliliter solution.

The at least one stabilizing compound bearing at least one thiol functional group, which is preferably monothioglycerol, may comprise 0.01 to 5 mg, preferably 0.015 to 1 mg, most preferably 0.1 mg per milliliter solution.

The at least one stabilizing compound selected from the group consisting of Thiamine salts, which is preferably Thiamine HCl, may comprise 0.01 to 5 mg, preferably 0.015 to 1 mg, most preferably 0.1 mg per milliliter solution.

Advantageously, the solution is in the form of a unit dose that does not exceed 100 milliliters.

The inventor has found a way to prepare a stable aqueous solution comprising at least one stabilizing-dissolving compound for paracetamol in solution selected from the group consisting of cyclodextrins, at least one stabilizing compound bearing at least one thiol functional group and at least one stabilizing compound selected from the group consisting of Thiamine salts in a suitable concentration, which is not only capable of having a concentration of paracetamol of more than 10 mg per milliliter of solution, but is also stable and does not need to be refrigerated when packed in clear glass sealed vials, or in stoppered glass vials or in bottles made of a polymer material such as polyethylene, or in soft material bags made from polyethylene, polyvinyl chloride or polypropylene. By "stable" is meant that the solution can be stored for at least 24 months at room temperature and at least 30 days at elevated temperature (70° C.) without the appearance of colour and particulate matter which is visible to the eye.

The use of the stabilizing-dissolving and stabilizing compounds according to the invention and preferably the chelating agent has been found to not only increase the paracetamol solubility to the extent that it is possible to dissolve 1000 mg of paracetamol into a final volume of 100 ml but also effectively stabilises the solution preventing the formation of particulate matter and colour at elevated temperature in ampoules, vials and bags.

The solution may be formulated in unit dose form, each unit dose containing from 100 mg to 1500 mg paracetamol inclusive, more preferably from 600 mg to 1000 mg inclusive, most preferably 1000 mg, in a volume not exceeding 100 milliliters.

The injectable stabilised solution of the invention may be prepared by methods known in the art.

The stabilised injectable solution of the invention may be packed into suitable containers known in the art (for example glass ampoules, vials, cartridges, glass sealed vials, or in stoppered glass vials or in bottles made of a polymer material such as polyethylene, or in soft material bags made from polyethylene, polyvinyl chloride or polypropylene). The glass should preferably be clear glass.

The stabilized injectable solution of the invention is suitable for intravenous use.

The stabilized injectable solution of the invention need not be stored under refrigerated conditions to provide a shelf life of at least 24 months, saving refrigeration costs during transport and storage, and alleviating patient discomfort during administration.

The invention will now be described in more detail with reference to the following non-limiting examples.

EXAMPLES

Example 1

A preferred pharmaceutical composition according to the invention comprises:

TABLE 1

| Ingredient | Quantity/100 ml |
| --- | --- |
| Paracetamol | 1000 mg |
| Hydroxypropyl-beta-cyclodextrin HPBCD | 666 mg |
| Monothioglycerol (MTG) | 10 mg |
| EDTA | 10 mg |
| Thiamine HCl | 10 mg |
| NaCl | 600 mg |
| Disodium phosphate dihydrate | 35.6 mg |
| Water for Injection to | 100 ml |
| Final pH (HCl or NaOH) 1M | 5.5-6.5 |

Example 2

The unit composition of a second formulation (Control, comparative example) is provided in Table 2 below:

TABLE 2

| Ingredient | Quantity/100 ml |
|---|---|
| Paracetamol | 1000 mg |
| Hydroxypropyl-beta-cyclodextrin HPBCD | 666 mg |
| Monothioglycerol (MTG) | 10 mg |
| EDTA | 10 mg |
| NaCl | 600 mg |
| Disodium phosphate dihydrate | 35.6 mg |
| Water for Injection to | 100 ml |
| Final pH (HCl or NaOH) 1M | 5.5-6.5 |

Example 3

Laboratory-scale formulations given in Examples 1 and 2 of the present invention were manufactured and filled into clear glass vials and polymer material (soft material bags) and placed on a stability program. Tables 3-4 below summarize the results obtained:

TABLE 3

Stability of 1000 mg/100 ml (Paracetamol-HPBCD) Batches at 70° C. for 20 days

| Example | Chemical stability | Appearance | Comments |
|---|---|---|---|
| Example 1 | Acceptable level of known degradant | Stable, clear solution | Complies, trial continued |
| Control Example 2 | Acceptable level of known degradant | Yellow color | Not stable, trial continued to 30 days as control |

TABLE 4

Stability of 1000 mg/100 ml (Paracetamol-HPBCD) Batches at 70° C. for 30 days

| Example | Chemical stability | Appearance | Comments |
|---|---|---|---|
| Example 1 | Acceptable level of known degradant | Stable, clear solution | Complies, trial continued |
| Control Example 2 | Acceptable level of known degradant | Yellow color | Not stable, trial continued to 40 days as control |

After 40 Days at 70° C. the solution according to example 1 still remained clear and colourless (both in clear glass vials and soft material bags), free from visible particulate matter.

Tables 3-4 show stability evaluations of 1000 mg per 100 ml paracetamol formulations and the solution according to the invention shows advantages over a control solution with a different composition of stabilizing compound.

Example 4

To produce 100 1000 mg/100 ml paracetamol units for IV injection, 8000 ml water for injection (WFI) is purged with nitrogen gas to reduce the oxygen. The water was heated to 50° C. Processing continues under a nitrogen gas blanket. 66.675 g of HPBCD (DS 4.69) is added to 60% of the WFI batch volume and is mixed until dissolved. The solution is then allowed to cool to room temperature. The solution is pre-filtered with a 0.45 Pg filter, followed by the addition of 1 g MTG, 1 g EDTA, 60 g NaCl, 1 g Thiamine HCl and 3.56 g Disodium phosphate dihydrate. The solution is stirred until all the MTG, EDTA, NaCl, Thiamine HCl and Disodium phosphate dihydrate is dissolved. The pH is then adjusted to 6 with HCl 1M. 100 g paracetamol is added to the solution and stirred until dissolved. pH is adjusted to 6, should it be required and made up to 100% volume with WFI. The resultant 1000 mg/100 ml paracetamol solution is sterilized by filtration with 0.22 Pm filters and filled into pre-sterilized vials or bags, under aseptic conditions. The vials or bags are sealed aseptically under nitrogen. The formulation contains 1000 mg/100 ml paracetamol, as determined by validated HPLC.

The invention claimed is:

1. A stable aqueous paracetamol solution for use in IV infusion comprising at least one stabilizing-dissolving compound for paracetamol in solution selected from the group consisting of cyclodextrins, at least one stabilizing compound bearing at least one thiol functional group and at least one stabilizing compound selected from the group consisting of thiamine salts.

2. The stable aqueous solution of claim 1, wherein the at least one stabilizing-dissolving compound for paracetamol in solution selected from the group consisting of cyclodextrins, the at least one stabilizing compound bearing at least one thiol functional group and the at least one stabilizing compound selected from the group consisting of thiamine salts are present in a total concentration between 0.001% m/v and 20% m/v.

3. The stable aqueous solution of claim 1, wherein the at least one stabilizing-dissolving compound for paracetamol in solution is selected from the group consisting of hydroxyalkyl-beta-cyclodextrins.

4. The stable aqueous paracetamol solution of claim 1, wherein the at least one stabilizing-dissolving compound for paracetamol in solution is 2-hydroxypropyl-beta-cyclodextrin.

5. The stable aqueous solution of claim 1, wherein the concentration of the at least one stabilizing-dissolving compound for paracetamol in solution is between 0.2% m/v and 19% m/v.

6. The stable aqueous paracetamol solution of claim 1, wherein the at least one stabilizing compound bearing at least one thiol functional group is selected from the group consisting of thioglycerols, cysteine, acetylcysteine, thioglycolic acid, salts of thioglycolic acid, dithiothreitol, reduced glutathione, thiolactic acid, salts of thiolactic acid, thiourea and mercaptoethanesulfonic acid.

7. The stable aqueous paracetamol solution of claim 1, wherein the at least one stabilizing compound bearing at least one thiol functional group is a thioglycerol.

8. The stable aqueous paracetamol solution of claim 1, wherein the at least one stabilizing compound bearing at least one thiol functional group is present in a concentration between 0.001% m/v and 0.2% m/v.

9. The stable aqueous paracetamol solution of claim 1, wherein the at least one stabilizing compound selected from the group consisting of thiamine salts is thiamine HCl.

10. The stable aqueous paracetamol solution of claim 1, wherein at least one stabilizing compound selected from the group consisting of thiamine salts is present in a concentration between 0.001% m/v and 0.2% m/v.

11. The stable aqueous paracetamol solution of claim 1, further comprising a chelating agent.

12. The stable aqueous paracetamol solution of claim 11, wherein the chelating agent is selected from the group consisting of EDTA, nitrilotriacetic acid, ethylenediamine-N,N'- diacetic-N,N'-dipropionic acid, ethylenediamine-tetra(methylene phosphoric acid), 2,2'(ethylenediamino)-dibutyric acid, ethylene glycol bis(2-aminoethylether)-N,N,N',N'-tetra acetic acid, and salts thereof.

13. The stable aqueous paracetamol solution of claim 11, wherein the chelating agent is present in a concentration between 0.001% m/v and 0.2% m/v.

14. The stable aqueous paracetamol solution of claim 1, wherein the pH is between 4.0 and 7, and the solution is buffered with a buffer composition selected from at least one of the acid form and the ionized form of: citric, malic, acetic, sorbic, phosphoric, fumaric, lactic, gluconic and tartaric acids or mixtures thereof.

15. The stable aqueous paracetamol solution of claim 1, wherein the concentration of paracetamol is between 0.20% m/v and 10% m/v.

16. The stable aqueous solution of claim 5, wherein the concentration of the at least one stabilizing-dissolving compound for paracetamol in solution is between 0.2% m/v and 6.0% m/v.

17. The stable aqueous solution of claim 5, wherein the concentration of the at least one stabilizing-dissolving compound for paracetamol in solution is between 0.5% m/v and 3.0% m/v.

18. The stable aqueous paracetamol solution of claim 7, wherein the at least one stabilizing compound bearing at least one thiol functional group is monothioglycerol.

19. The stable aqueous paracetamol solution of claim 14, wherein the buffer composition is disodium phosphate dihydrate.

20. The stable aqueous paracetamol solution of claim 15, wherein the concentration of paracetamol is between 0.5% m/v and 1.5% m/v.

* * * * *